(12) United States Patent
Ozawa et al.

(10) Patent No.: US 7,120,227 B2
(45) Date of Patent: Oct. 10, 2006

(54) METHOD OF DISPLAYING DYNAMICALLY SCATTERING VECTOR OF X-RAY DIFFRACTION

(75) Inventors: Tetsuya Ozawa, Hino (JP); Susumu Yamaguchi, Hamura (JP); Kohji Kakefuda, Akishima (JP)

(73) Assignee: Rigaku Corporation, Tokyo (JP)

( * ) Notice: Subject to any disclaimer, the term of this patent is extended or adjusted under 35 U.S.C. 154(b) by 59 days.

(21) Appl. No.: 10/854,562

(22) Filed: May 25, 2004

(65) Prior Publication Data
US 2005/0002488 A1    Jan. 6, 2005

(30) Foreign Application Priority Data
May 29, 2003   (JP)   ............... 2003-153496

(51) Int. Cl.
*G01N 23/201*   (2006.01)

(52) U.S. Cl. .......................... 378/87; 378/80
(58) Field of Classification Search ................. 378/87, 378/73, 70, 80
See application file for complete search history.

(56) References Cited

U.S. PATENT DOCUMENTS 6,198,796 B1 *   3/2001   Yokoyama et al. ............ 378/73
2003/0009316 A1 *   1/2003   Yokoyama et al. ............ 703/2

FOREIGN PATENT DOCUMENTS

| EP | 0 959 345 A | 11/1999 |
| EP | 0 962 762 A | 12/1999 |
| JP | 2000-039409 A | 2/2000 |

* cited by examiner

*Primary Examiner*—David V. Bruce
*Assistant Examiner*—Hoon Song
(74) *Attorney, Agent, or Firm*—Frishauf, Holtz, Goodman & Chick, PC

(57) ABSTRACT

The scattering vector of X-ray diffraction is dynamically displayed on a screen. A dynamic motion and tracks of the tip location of the scattering vector of X-ray diffraction is displayed two-dimensionally or three-dimensionally under changing measuring conditions on a screen which represents the reciprocal space of a sample crystal. The tip location of the scattering vector can be seen dynamically and the X-ray diffraction phenomenon under changing measuring conditions can be readily understood, effecting easy consideration of the measuring conditions and easy evaluation of the measured results.

7 Claims, 8 Drawing Sheets

METHOD OF DISPLAYING DYNAMICALLY SCATTERING VECTOR OF X-RAY DIFFRACTION

BACKGROUND OF THE INVENTION

1. Field of the Invention

The present invention relates to a method of dynamically displaying a motion of the tip location of a scattering vector of X-ray diffraction.

2. Description of the Related Art

The scattering vector of X-ray diffraction is a concept which has been introduced to explain theoretically the X-ray diffraction phenomenon. The scattering vector is helpful in understanding the X-ray diffraction phenomenon. The scattering vector is indeed useful in considering measuring conditions and in interpreting measured results in the actual X-ray diffraction measurement procedure. Although the scattering vector is a useful concept as described above, its direction and magnitude are invisible because the scattering vector is an imaginary existence which is defined by the relative location among an X-ray source, a sample and an X-ray detector.

A certain prior art has been developed which makes it possible to display such scattering vector on a screen. The prior art is disclosed in Japanese patent publication No. 2000-39409 A, in which when the measuring conditions of X-ray diffraction are selected, the scattering vector can be displayed on a screen which represents a reciprocal space.

Although such prior art can display the scattering vector on the screen representing the reciprocal space, the prior art can display neither motion of the scattering vector nor tracks of the motion. It would be out of the usual to select only one measuring condition for detecting an X-ray diffraction intensity in carrying out the X-ray diffraction measurement. It would be usual to collect a plurality of diffraction intensity data under different measuring conditions so that the data can be combined with each other to make any analysis or evaluation. Therefore, if there exists a certain technology which makes it possible to understand how the scattering vector changes depending on the change in measuring conditions, such technology must be very helpful in considering the measuring conditions and in evaluating the measured results. An apparatus realizing such technology, however, has not been found.

SUMMARY OF THE INVENTION

It is an object of the present invention to provide a method of dynamically displaying the scattering vector of X-ray diffraction.

A method according to the present invention comprises a step of displaying two-dimensionally or three-dimensionally a dynamic motion and tracks of the tip location of a scattering vector of X-ray diffraction under changing measuring conditions on a display screen which represents the reciprocal space of a sample crystal. This invention has an advantage that the tip location of the scattering vector can be seen dynamically and the X-ray diffraction phenomenon under changing measuring conditions can be readily understood, effecting easy consideration of the measuring conditions and easy evaluation of the measured results.

It would be effective to carry out the dynamic display method in real time with X-ray diffraction measurement, so as to understand visually what diffraction measurement is now progressing.

The dynamic display method is usable for a dynamic simulation, in which (1) an operator enters measuring conditions into a measuring-condition setting device, (2) a control device acquires the measuring conditions, and (3) the control device puts the virtual scattering vector in motion on a display screen based on the measuring conditions acquired. The dynamic display method is for showing neither the movement of a visible X-ray detector nor a visible sample but the motion of the scattering vector in the reciprocal space dynamically, the scattering vector being invisible actually but representing importantly the nature of the X-ray diffraction phenomenon. The method of the present invention is therefore best suited for the study of measuring conditions. Furthermore, the dynamic display method is effective in showing the X-ray diffraction phenomenon visually for persons not familiar with the X-ray diffraction.

In another case, the measuring-condition setting device can acquire the measuring conditions under which the measurement has been completed so as to dynamically display the scattering vector which has been used, helpful in understanding the measured results.

It is useful to display information about an X-ray diffraction intensity along with the tracks of the tip location of the scattering vector. The intensity information can be expressed by the color or width of the tracks on the display screen, for example.

It is also useful to superimpose the locations of the reciprocal lattice points on the tracks. The X-ray diffraction principle suggests that when the tip location of the scattering vector coincides with any reciprocal lattice point, an X-ray diffraction phenomenon occurs at the crystal lattice plane corresponding to the reciprocal lattice point. Therefore, observing the superposition of the locations of the reciprocal lattice points on the tracks makes it possible to determine whether or not X-ray diffraction occurs on the tracks.

DESCRIPTION OF THE PREFERRED EMBODIMENTS

Figure 1:
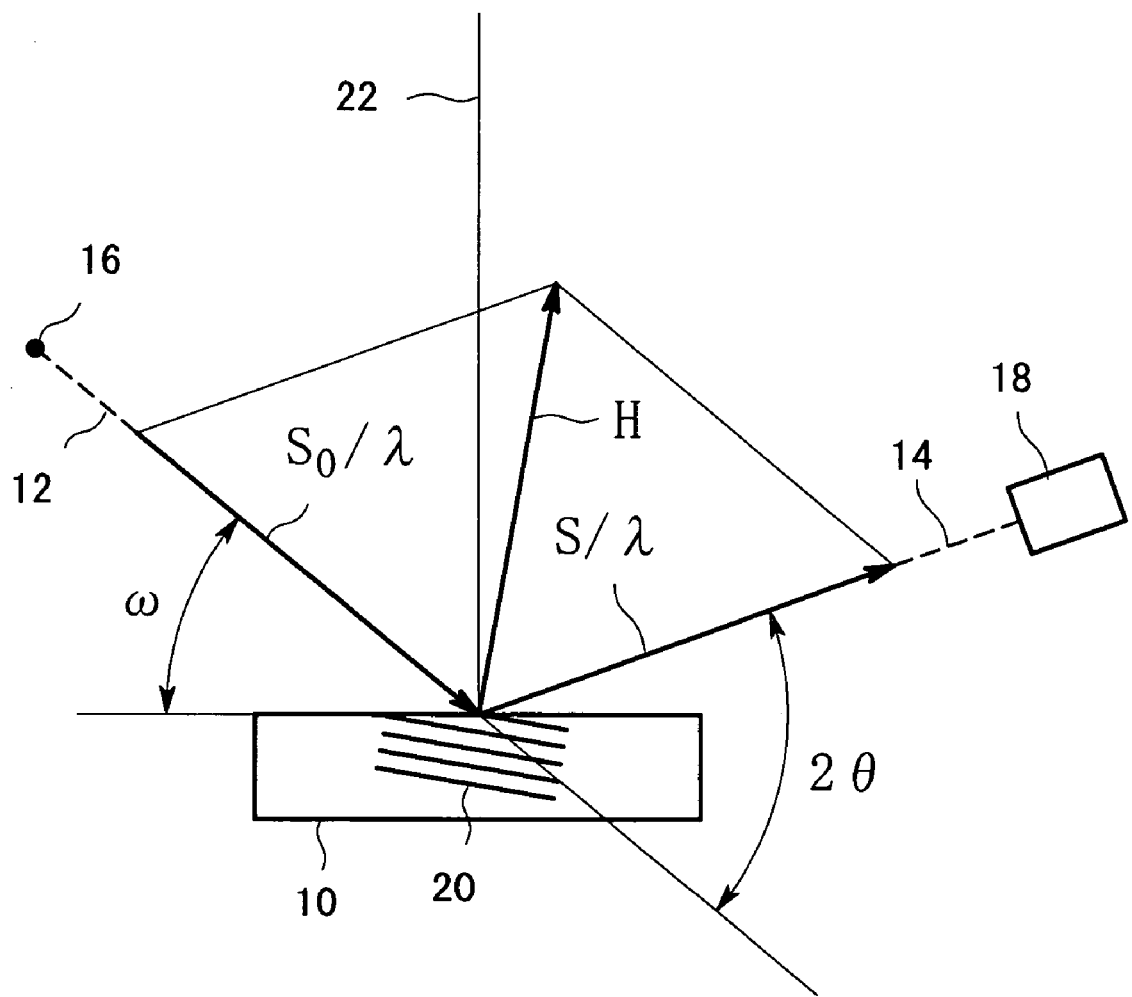
FIG. 1 is an explanatory view of the scattering vector of X-ray diffraction.

An embodiment of the present invention will be described with reference to the drawings. First of all, the scattering vector will be explained. FIG. 1 is a view for explaining the scattering vector H of X-ray diffraction, in which an X-ray 12 is incident on the surface of a sample 10, and a diffracted X-ray 14 goes out of the sample surface. An angle of the incident X-ray 12 to the surface of the sample 10 is referred to as an incident angle which is denoted by $\omega$, and an angle of the diffracted X-ray 14 to the incident angle 12 is referred to as a diffraction angle which is denoted by $2\theta$. In the X-ray diffraction measurement, the incident X-ray 12 comes from an X-ray source 16, and the diffracted X-ray 14 is to be detected by an X-ray detector 18.

An X-ray diffraction phenomenon will be explained with the use of the reciprocal space of the crystal which makes up the sample 10. A unit vector $S_0$ is taken as extending in the direction of the incident X-ray 12, and another unit vector S is taken as extending in the direction of the diffracted X-ray 14. Assuming that an incident X-ray vector is defined as $S_0/\lambda$ and a diffracted X-ray vector is defined as $S/\lambda$ where $\lambda$ is the wavelength of an X-ray, vectorial subtraction of the incident X-ray vector from the diffracted X-ray vector becomes, as well known, the scattering vector H. The X-ray diffraction principle suggests that when the tip location of the scattering vector H coincides with any lattice point in the reciprocal space, X-ray diffraction occurs at the real lattice plane 20, which is a crystal lattice plane in the real space, corresponding to the reciprocal lattice point. The scattering vector H has the property that the direction is perpendicular to the real lattice plane 20 and the magnitude is equal to the inverse number of the lattice spacing of the real lattice plane 20.

Figure 2:
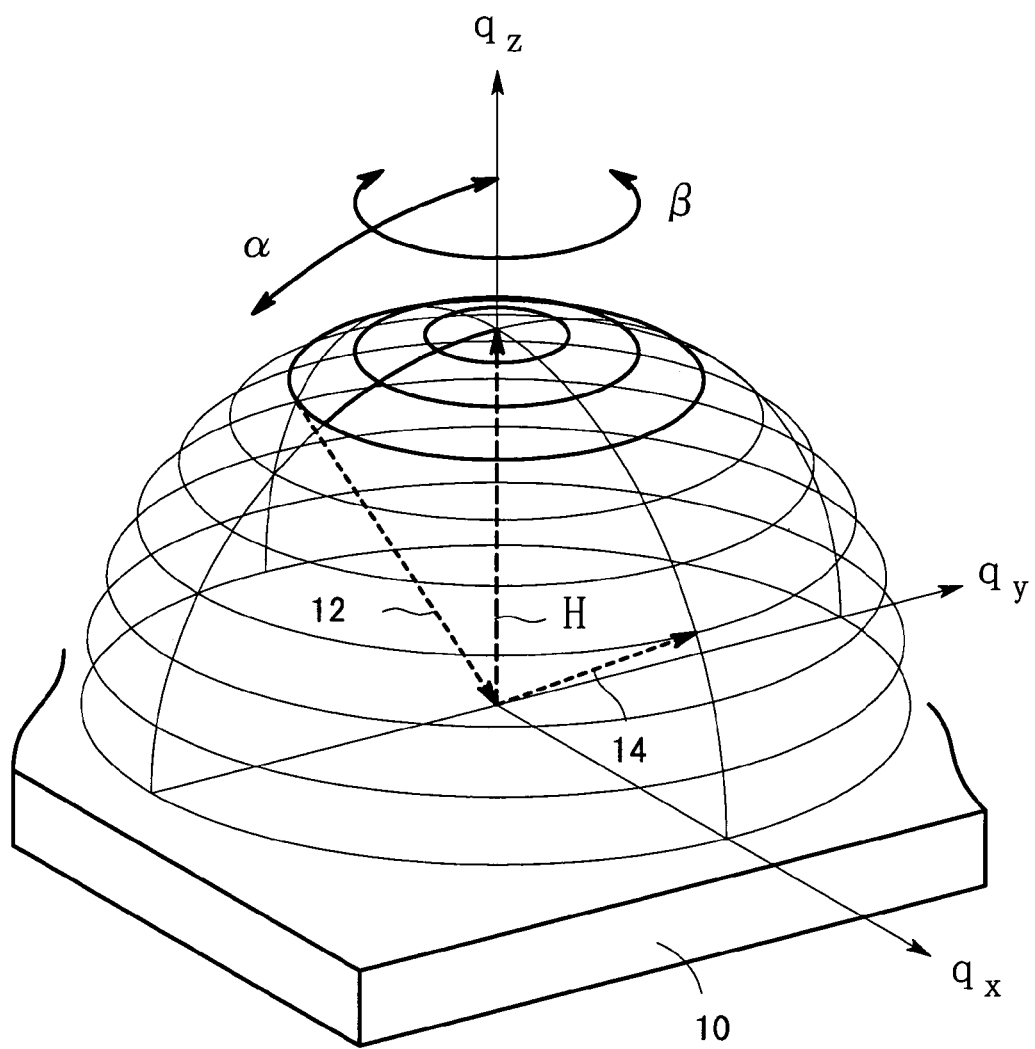
FIG. 2 shows an example of a picture on a screen in which the dynamic display method according to the invention is applied to the pole figure measurement.

FIG. 2 shows one example of a screen image in which the dynamic display method according to the invention is applied to the pole figure measurement. The screen image indicates the reciprocal space of the crystal which makes up the sample 10. An orthogonal coordinate system including qx, qy and qz in the reciprocal space defines a three-dimensional space. If the sample crystal is tetragonal or cubic, the reciprocal space becomes a three-dimensional orthogonal coordinate system, in which a qz-axis is defined as extending in the normal direction of the sample surface and a qx-axis and a qy-axis are defined as being on the sample surface.

In the case of the pole figure measurement, measuring conditions are selected to become a combination of (1) a setting condition in which the X-ray diffraction optical system, which includes the incident X-ray 12 and the diffracted X-ray 14, is inclined to a direction of an angle $\alpha$ shown in FIG. 2 on the basis of the sample 10 and (2) another setting condition in which the X-ray diffraction optical system is rotated around the normal of the sample 10, which coincides with the qz-axis, by an angle $\beta$. In FIG. 2, an angle of the diffracted X-ray 14 to the incident X-ray 12, i.e., a diffraction angle $2\theta$, is set to 60 degrees. The angle $\alpha$ is selected to range from zero degree, i.e., the condition in which the scattering vector H coincides with the normal of the sample surface, to 30 degrees at ten-degree intervals. The angle $\alpha$ is selected to range from zero to 360 degrees at five-degree intervals. The motion tracks of the tip location of the scattering vector are represented as heavy full lines in FIG. 2 under the measuring conditions made of combinations of $\alpha$ and $\beta$.

Figure 6:
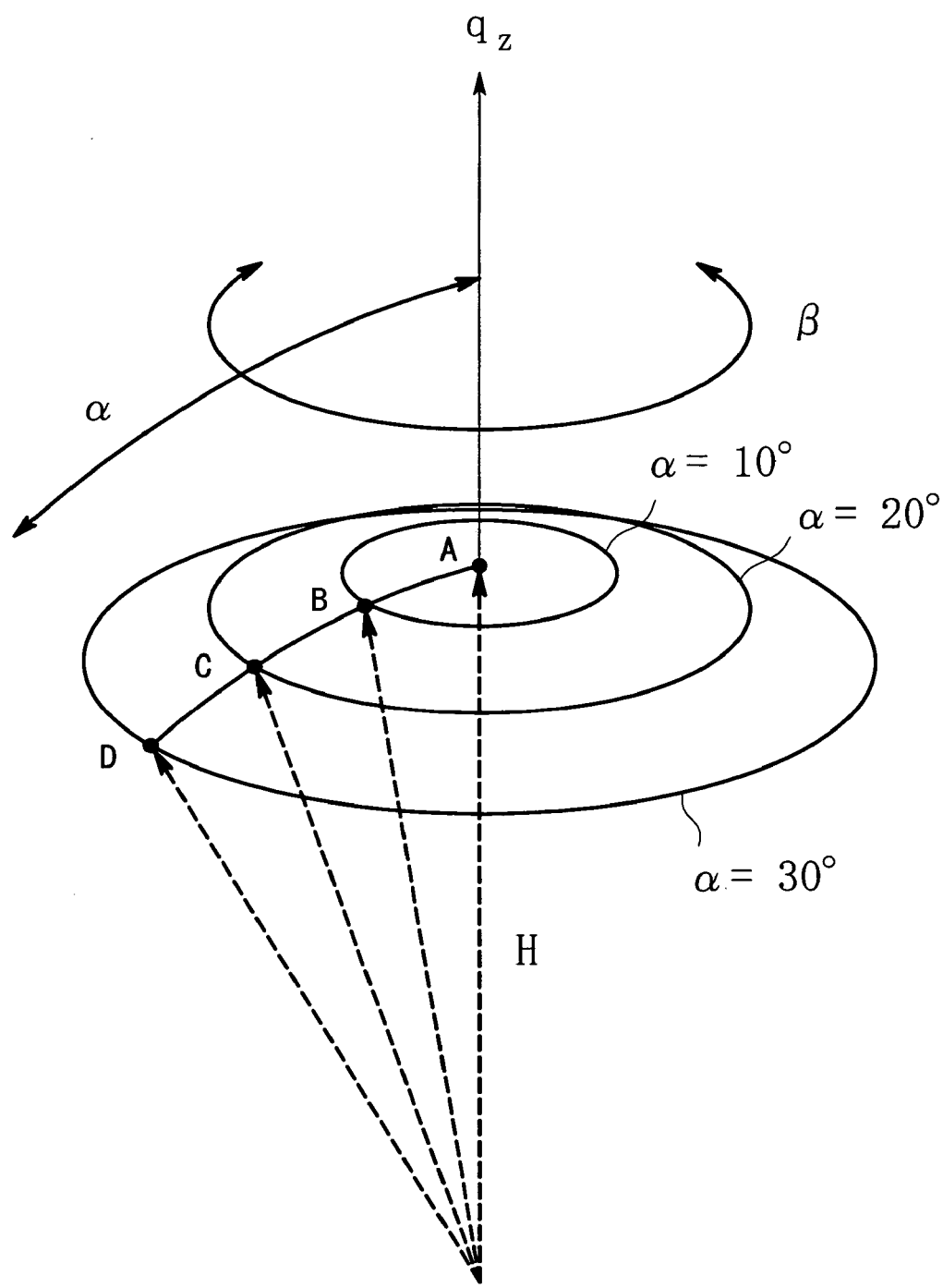
FIG. 6 is an enlarged view of a part of the picture shown in FIG. 2.

The motion of the tip location of the scattering vector will be explained in detail. FIG. 6 shows an enlarged view of a part of the screen image shown in FIG. 2. The tip of the scattering vector H has a place at a point A at the start of the measurement. X-ray diffraction measurement is carried out initially at this point, i.e., the intensity of a diffracted X-ray is detected. Then the X-ray diffraction optical system is inclined on the basis of the sample so that the angle $\alpha$ becomes 10 degrees and the tip of the scattering vector H has a place at a point B, noting however that in the actual apparatus the sample may be inclined while the X-ray diffraction optical system may be held stationary. With the angle $\alpha$ being held this value, the angle $\beta$ is changed stepwise at five-degree intervals from zero to 360 degrees, so that X-ray diffraction measurement is carried out for seventy-two values of $\beta$. During the seventy-two operations of the X-ray diffraction measurement, the scattering vector H rotates around the qz-axis with one revolution and returns to the point B with the angle $\alpha$ being held 10 degrees. Next, the angle $\alpha$ is changed to 20 degrees and the angle $\beta$ is changed at five-degree intervals so as to carry out X-ray diffraction measurement. FIG. 6 shows the tracks of the tip location of the scattering vector H after completion of the measurement under the condition of the angle $\alpha$ ranging from zero to 30 degrees. Stating in detail, the tip location of the scattering vector H starts from the point A, and moves to the point B, and rotates around the qz-axis with one revolution back to the point B, and moves to a point C, and rotates around the qz-axis with one revolution back to the point C, and moves to a point D, and rotates around the qz-axis with one revolution back to the point D to complete the measurement.

As described above, the motion of the tip location of the scattering vector H can be displayed on a screen in real time during the pole figure measurement, and the tracks of the motion remains displayed on the screen. Accordingly, an operator of the pole figure measurement can understand in real time where the tip location of the scattering vector H is at the moment.

The tracks can be displayed on the screen even if the X-ray diffraction measurement is not carried out. That is, the operator can enter the measuring conditions made of many combinations of $\alpha$ and $\beta$ into the measuring-condition setting device, so that the motion of the tip location of the scattering vector and the tracks of the motion can be dynamically displayed without X-ray diffraction measurement.

Figure 3:
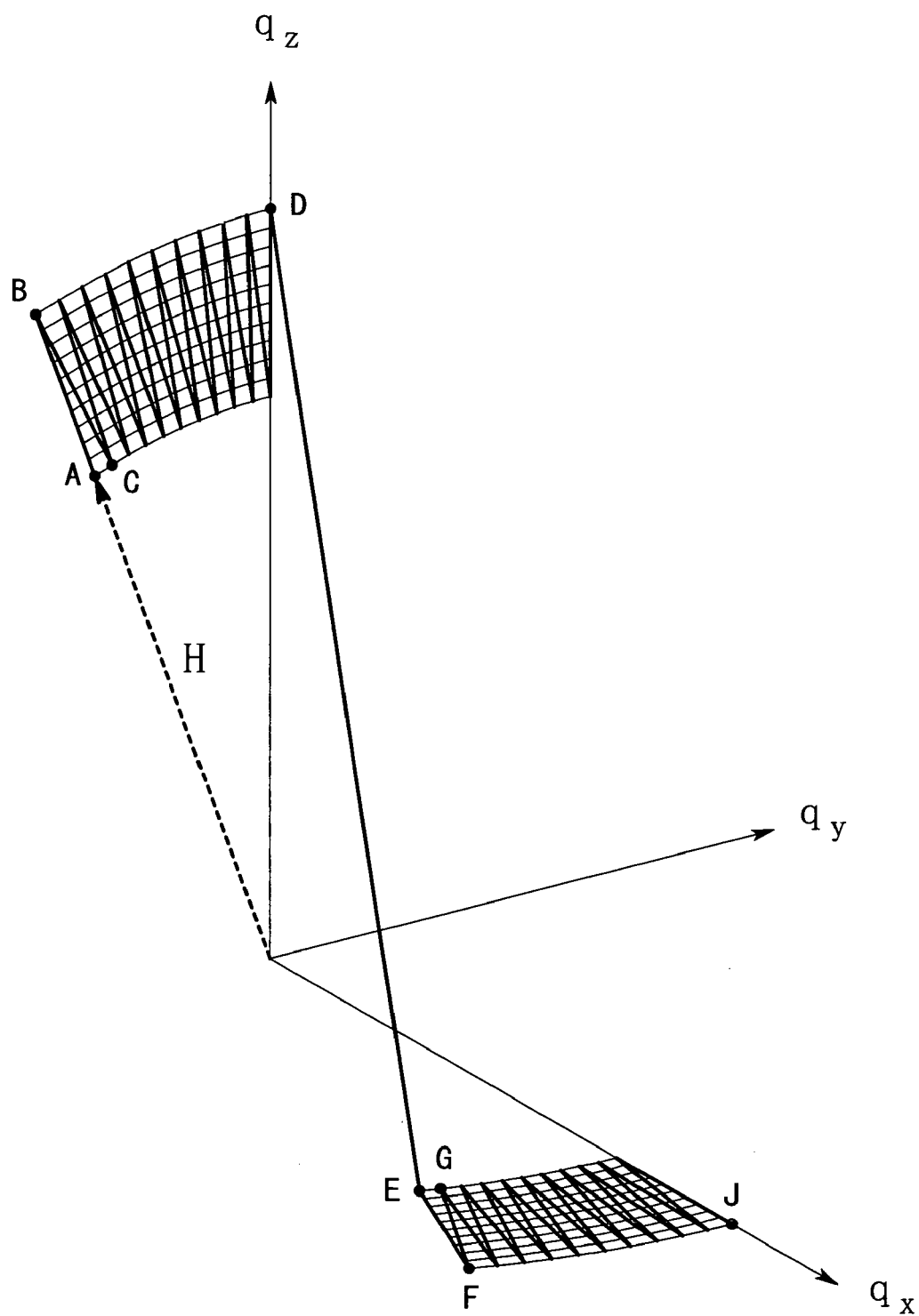
FIG. 3 shows an example of a picture on a screen in which the dynamic display method according to the invention is applied to the reciprocal-space mapping measurement.

Next, another example of display will be described. FIG. 3 shows an example of a picture on a screen in which the dynamic display method according to the invention is applied to the reciprocal-space mapping measurement. The picture shows dynamically the motion of the tip location of the scattering vector and the motion tracks in the case of a series of operations of (1) reciprocal-space mapping measurement within a plane perpendicular to the sample surface, referred to hereinafter as out-of-plane reciprocal-space mapping, and (2) reciprocal-space mapping measurement with a plane including the sample surface, referred to hereinafter as in-plane reciprocal-space mapping. The out-of-plane reciprocal-space mapping measurement is carried out under the measuring conditions described below. The center of the mapping is 60 degrees in $2\theta$ and 20 degrees in $\omega$, the $2\theta/\omega$ is selected to range from 50 to 70 degrees at two-degree intervals, and the $\Delta\omega$ is selected to range from minus 10 to plus 10 degrees at two-degree intervals, noting that the definition of $2\theta$ and $\omega$ is shown in FIG. 1. On the other hand, the in-plane reciprocal-space mapping measurement is carried out under the conditions that the center of the mapping is 60 degrees in $2\theta\chi$ and 20 degrees in $\phi$, the $2\theta\chi/\phi$ is selected to range from 50 to 70 degrees at two-degree intervals, and the $\Delta\phi$ is selected to range from minus 10 to plus 10 degrees at two-degree intervals, noting that the angle $\phi$ is an angle of in-plane rotation of the sample and the angle $2\theta\chi$ is a diffraction angle corresponding to $2\theta$ in the out-of-plane diffraction.

The tip location of the scattering vector H starts from a point A which is minus 10 degrees in $\Delta\omega$ and 50 degrees in $2\theta/\omega$. The tip location then moves from this point to a point B, which is the same as the point A in $\Delta\omega$ and 70 degrees in $2\theta/\omega$, such a movement being referred to as a $2\theta/\omega$ scan. Eleven operations of X-ray diffraction measurement are carried out at two-degree intervals in $2\theta/\omega$. During the X-ray measurement, an operator looking at the screen will observe that the tip location of the scattering vector H is moving from the point A to the point B, the direction of the scattering vector H being unchanged. Next, the tip location of the scattering vector H moves from the point B to a point C, i.e., $\Delta\omega$ is set at minus eight degrees and $2\theta/\omega$ is returned to 50 degrees. Then the $2\theta/\omega$ scan is carried out again from the point C so as to prosecute additional eleven operations of X-ray diffraction measurement similarly. Such procedures are carried out for eleven values of $\Delta\omega$ ranging from minus 10 to plus 10 degrees. The final location of the out-of-plane reciprocal-space mapping measurement has a place of a point D. The frequency of the measurement operations runs up eleven times eleven being a hundred and twenty one.

Next, the procedure moves to the in-plane reciprocal-space mapping measurement. The tip location of the scattering vector H at the point D now moves drastically to a point E which is on the sample surface, the point E being minus 10 degrees in $\Delta\phi$ and 50 degrees in $2\theta\chi/\phi$. The tip location then moves from this point to a point F, which is the same as the point E in $\Delta\phi$ and 70 degrees in $2\theta\chi/\phi$, so as to carry out eleven measurement operations of X-ray diffraction at two-degree intervals in $2\theta\chi/\phi$, such a movement being referred to as a $2\theta\chi/\phi$ scan. During the measurement, an operator looking at the screen will observe that the tip location of the scattering vector H is moving from the point E to the point F with the direction of the scattering vector H unchanged. Next, the tip location of the scattering vector H jumps from the point F to a point G, i.e., $\Delta\phi$ is changed to minus eight degrees and $2\theta/\omega$ is returned to 50 degrees. Then the $2\theta\chi/\phi$ scan is carried out again from the point G so as to prosecute additional eleven operations of X-ray diffraction measurement similarly. Such procedures are carried out with eleven values of $\Delta\phi$ ranging from minus 10 degrees to plus 10 degrees. The final location of the in-plane reciprocal-space mapping measurement has a place of a point J. The frequency of the measurement operations in the in-plane reciprocal-space mapping also runs up eleven times eleven being a hundred and twenty one.

A series of operations regarding the out-of-plane and the in-plane reciprocal-space mapping measurement have now been completed. The motion tracks of the tip location of the scattering vector remains in the screen as shown in FIG. 3.

If the measurement procedures come to an end after completion of the out-of-plane reciprocal-space mapping measurement only, the tip location of the scattering vector is to move within the qy-qz plane only, it being sufficient to display only a two-dimensional reciprocal space for the tack indication of the tip location of the scattering vector. Similarly, if the measurement procedures are carried out for the in-plane reciprocal-space mapping only, the tip location of the scattering vector is to move within the qx-qy plane only, it being sufficient to display only a two-dimensional reciprocal space alike.

Figure 4:
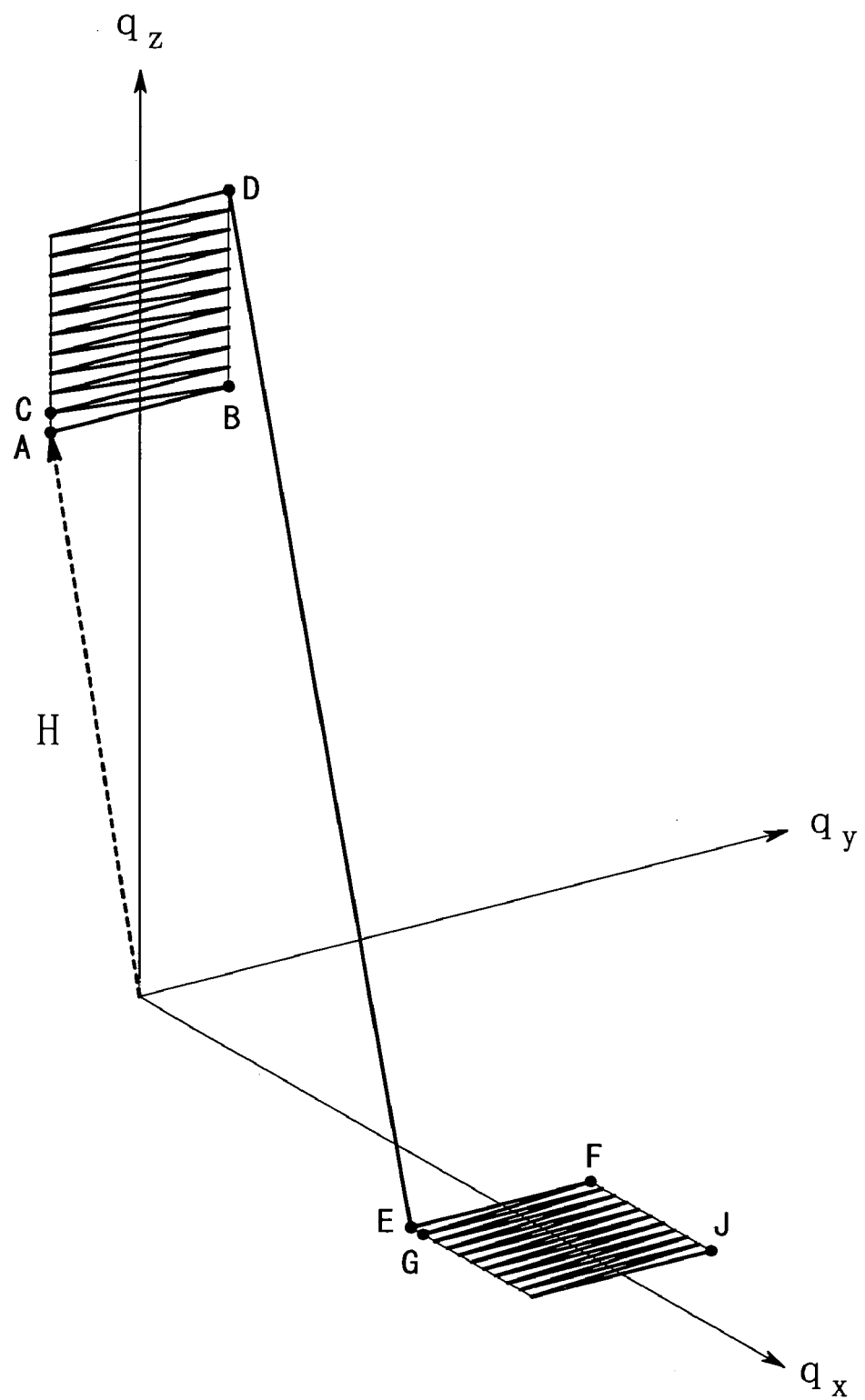
FIG. 4 shows an example of a picture on a screen in which the dynamic display method according to the invention is applied to the mesh measurement.

FIG. 4 shows an example of a picture on a screen in which the dynamic display method according to the invention is applied to mesh measurement. The picture shows dynamically the motion of the tip location of the scattering vector and the motion tracks in the case of a series of operations for (1) mesh measurement within a plane perpendicular to the sample surface, referred to hereinafter as out-of-plane mesh measurement, and (2) mesh measurement within a plane including the sample surface, referred to hereinafter as in-plane mesh measurement. The out-of-plane mesh measurement is carried out under the measuring conditions described below. The center of the mesh measurement is located at zero in qy and 0.8 in qz. The value of $\Delta qy$ is selected to range from minus 0.1 to plus 0.1 at 0.02 intervals on the basis of the center position mentioned above, and $\Delta qz$ is selected to range from minus 0.1 to plus 0.1 at 0.02 intervals similarly, noting that the measures of qy and qz are the inverse number of angstrom and also the measure of qx is the same. On the other hand, the in-plane mesh measurement is carried out under the conditions in which the center of the mesh measurement is located at zero in qy and 0.8 in qx. The value of $\Delta qx$ is selected to range from minus 0.1 to plus 0.1 at 0.02 intervals and $\Delta qy$ is selected to range from minus 0.1 to plus 0.1 at 0.02 intervals similarly.

The tip location of the scattering vector H starts from a point A which is minus 0.1 in $\Delta qy$ and minus 0.1 in $\Delta qz$. The tip location then moves from this point to a point B, which is the same as the point A in $\Delta qz$ and plus 0.1 in $\Delta qy$, so as to carry out eleven measurement operations of X-ray diffraction at 0.02 intervals in $\Delta qy$, such a movement being referred to hereinafter as a qy scan. During the measurement, an operator looking at the screen will observe that the tip location of the scattering vector H is moving horizontally rightward from the point A to the point B. Next, the tip location of the scattering vector H jumps from the point B to a point C, i.e., $\Delta qz$ is changed to minus 0.08 and $\Delta qy$ is returned to minus 0.1. Then the qy scan is carried out again from the point C so as to prosecute additional eleven operations of X-ray diffraction measurement similarly. Such procedures are carried out for eleven values of $\Delta qz$ ranging from minus 0.1 to plus 0.1. The final location of the out-of-plane mesh measurement has a place of a point D. The frequency of the measurement operations runs up eleven times eleven being a hundred and twenty one.

Next, the procedure moves to the in-plane mesh measurement. The tip location of the scattering vector H at the point D now moves drastically to a point E which is on the sample surface, the point E being minus 0.01 in $\Delta qx$ and minus 0.01 in $\Delta qy$. The tip location then moves from this point to a point F, which is the same as the point E in $\Delta qx$ and plus 0.1 in $\Delta qy$, so as to carry out eleven measurement operations of X-ray diffraction at 0.02 intervals in $\Delta qy$, such movement being referred to also as the qy scan. During the measurement, an operator looking at the screen will observe that the tip location of the scattering vector H is moving horizontally rightward from the point E to the point F within the sample surface. Next, the tip location of the scattering vector H jumps from the point F to a point G, i.e., $\Delta qx$ is changed to minus 0.08 and $\Delta qy$ is returned to minus 0.1. Then the qy scan is carried out again from the point G so as to prosecute additional eleven operations of X-ray diffraction measurement similarly. Such procedures are carried out for eleven values of $\Delta qx$ ranging from minus 0.1 to plus 0.1. The final location of the in-plane mesh measurement has a place of a point J. The frequency of the measurement operations for the in-plane mesh measurement also runs up eleven times eleven being a hundred and twenty one.

A series of operations regarding the out-of-plane and the in-plane mesh measurement have now been completed. The motion tracks of the tip location of the scattering vector remains in the screen as shown in FIG. 4.

Figure 5:
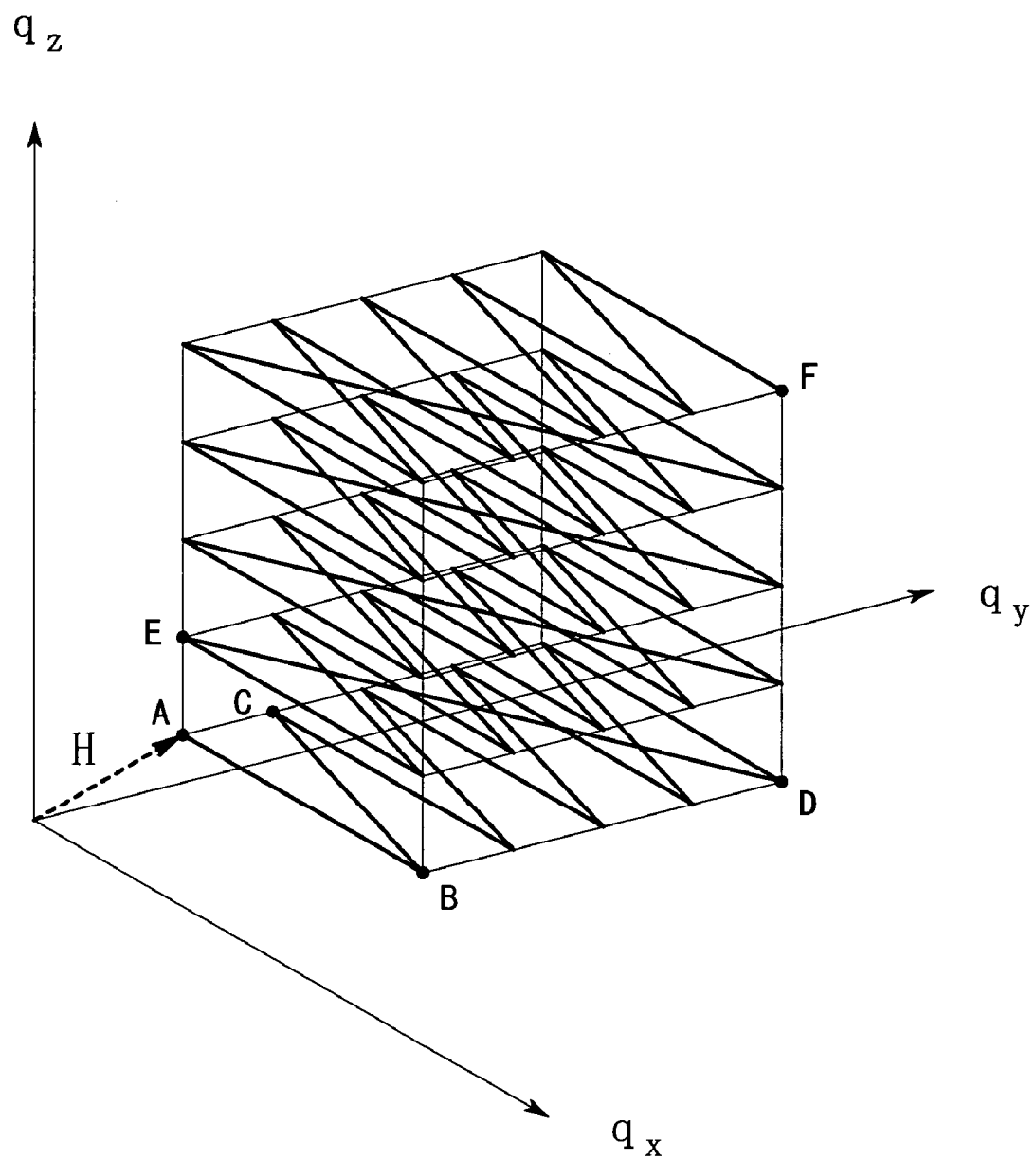
FIG. 5 shows an example of a picture on a screen in which the dynamic display method according to the invention is applied to the three-dimensional mesh measurement.

FIG. 5 shows an example of a picture on a screen in which the dynamic display method according to the invention is applied to three-dimensional mesh measurement, which is carried out under the measuring conditions described below. All the values of qx, qy and qx are selected to range from 0.1 to 0.5 at 0.1 intervals so as to prosecute operations of the X-ray diffraction measurement, noting that the measures of qx, qy and qz are the inverse number of angstrom. The frequency of the measurement operations runs up five times five times five being a hundred and twenty five.

The tip location of the scattering vector H starts from a point A which is 0.1 in qx, 0.1 in qy and 0.1 in qz. The tip location then moves from this point to a point B, which is the same as the point A in qy and qz and 0.5 in qx, so as to carry out five operations of X-ray diffraction measurement at 0.1 intervals in qx, such a movement being referred to hereinafter as a qx scan. Next, the tip location of the scattering vector H jumps from the point B to a point C, i.e., qy is changed to 0.2 and qx is returned to 0.1, noting that qz remains as it is. Then the qx scan is carried out again from the point C so as to prosecute additional five operations of X-ray diffraction measurement similarly. Such procedures are carried out for five values of qy ranging from 0.1 to 0.5. The tip location of the scattering vector reaches at a point D on completion of twenty-five operations, five times five, with qz remaining unchanged. Next, the tip location of the scattering vector H jumps from the point D to a point E, which is 0.1 higher in qz than the point A. Similar operations are carried for five values of qz ranging from 0.1 to 0.5. The final location has a place of a point F to complete the measurement, and the frequency of the measurement operations runs up a hundred and twenty five.

During the three-dimensional mesh measurement, an operator looking at the screen will observe that the tip location of the scattering vector H is moving regularly in the three-dimensional space. The motion tracks of the tip location of the scattering vector remains in the screen as shown in FIG. 5 on completion of the measurement.

The procedures of the X-ray diffraction measurement may be carried out with the continuous scan or the stepwise scan in scanning the measuring conditions for prosecuting the examples described above. The continuous scan is defined as to carry out each operation of the X-ray diffraction measurement during a continuous change in angle to be scanned. In contrast, the stepwise scan is defined as to carry out each operation of the X-ray diffraction measurement at a temporarily stationary angle to be scanned. In the case of the continuous scan, the obtained X-ray diffraction intensity should be taken as the data at the center position of the angle which changes during the measurement operation.

Figure 7:
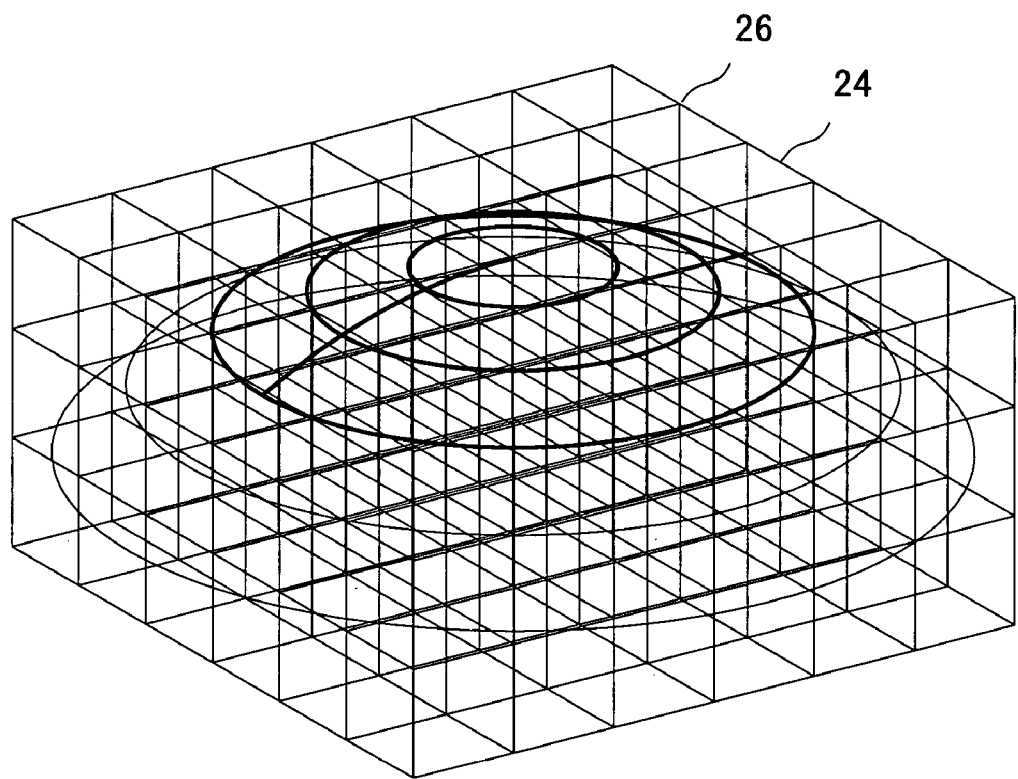
FIG. 7 shows superposition of the reciprocal lattice over the dynamic picture shown in FIG. 2.

The lattice points of the reciprocal lattice may be superimposed on a display of the motion and tracks of the tip location of the scattering vector in carrying out the present invention. FIG. 7 shows superposition of the reciprocal lattice over the dynamic picture shown in FIG. 2. The X-ray diffraction principle suggests that when the tip location of the scattering vector coincides with any lattice point in the reciprocal space, X-ray diffraction occurs at the real lattice plane corresponding to the reciprocal lattice point. An operator can perceive useful information from the superimposed picture shown in FIG. 7: for example, the tip location of the scattering vector is moving closer to one of the reciprocal lattice points or the tip location is just passing through one of the reciprocal lattice points. The superimposed picture is accordingly very helpful in understanding the status of the X-ray diffraction.

Although the lattice points 26 of the reciprocal space are expressed by intersections of many line segments 24 which passing through the lattice points 26, the expression is not to be considered limited to the intersections but the lattice points may be expressed by black spots or the like.

Figure 8A:
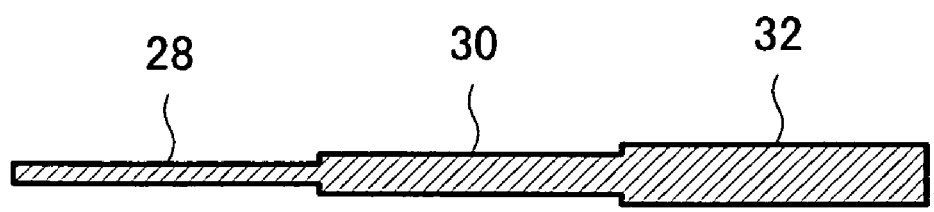
FIG. 8A is an explanatory view of the track line segment having a width which changes according to the diffraction intensity data.

Next, further another example will be described in which the tracks of the tip location of the scattering vector is accompanied by the diffraction intensity data. FIG. 8A shows an example in which the track line segment has a width which changes according to the diffraction intensity data. The track is expressed by a line segment 28 having a width corresponding to one pixel of the display screen when the intensity of a diffracted X-ray is less than the predetermined minimum value, including zero. The width varies with the intensity such that a line segment 30 with a higher intensity has a width corresponding to two pixels, and a line segment 32 with a further higher intensity has a width corresponding to three pixels. It can be seen accordingly from the picture on a screen how the diffraction intensity varies along the tracks of the tip location of the scattering vector.

Figure 8B:
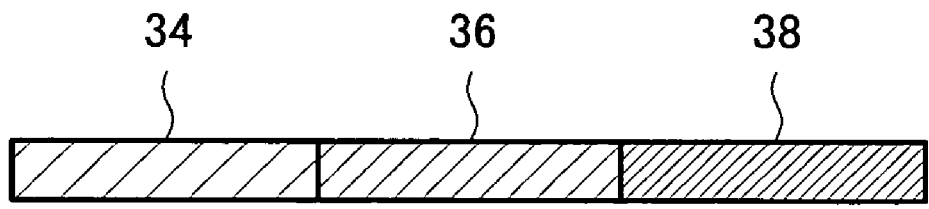
FIG. 8B is an explanatory view of the track line segment having a color which changes according to the diffraction intensity data.

FIG. 8B shows an example in which the track line segment has a color which changes according to the diffraction intensity data. The color varies with the intensity such that a line segment 34 has the first color, a line segment 36 has the second color and a line segment 38 has the third color. The color may be changed only in brightness with the same hue unchanged, i.e., the gray scale expression. Alternatively, the color may be changed in hue for a colorful expression.

What is claimed is:

1. A method of dynamically displaying a scattering vector of X-ray diffraction comprising a step of:
   displaying two-dimensionally or three-dimensionally a dynamic motion and tracks of a tip location of a scattering vector of X-ray diffraction under changing measuring conditions of X-ray diffraction on a display screen which represents a reciprocal space of a sample crystal.

2. A method according to claim 1, wherein said dynamic motion and tracks is displayed during X-ray diffraction measurement.

3. A method according to claim 1, wherein said displaying step includes:
   acquiring a change of measuring conditions from a measuring-condition setting device; and
   displaying said dynamic motion and tracks in accordance with said change of measuring conditions acquired.

4. A method according to claim 1, wherein said tracks is displayed along with information about an X-ray diffraction intensity.

5. A method according to claim 4, wherein said information is expressed in a color of said tracks.

6. A method according to claim 4, wherein said information is expressed in a width of said tracks.

7. A method according to claim 1, further comprising a step of superimposing locations of reciprocal lattice points on said tracks.

* * * * *